United States Patent [19]

Lacal et al.

[11] Patent Number: 4,820,631

[45] Date of Patent: Apr. 11, 1989

[54] DELETION MUTANTS AND MONOCLONAL ANTIBODIES AGAINST RAS PROTEINS

[75] Inventors: Juan C. Lacal, Bethesda, Md.; Stuart A. Aaronson, Vienna, Va.

[73] Assignee: The United States of America as represented by the Secretary of the Department of Health and Human Services, Washington, D.C.

[21] Appl. No.: 890,510

[22] Filed: Jul. 30, 1986

[51] Int. Cl.$^4$ .................. C12Q 1/68; G01N 33/53; G01N 33/577; C12N 5/00

[52] U.S. Cl. ........................................ 435/6; 435/7; 435/172.2; 435/810; 436/548; 436/813; 436/808; 530/387

[58] Field of Search ............... 435/172.1, 172.2, 6, 435/849, 7, 68, 240.27, 810; 436/548, 811, 63, 64, 813, 808; 530/350, 387; 935/110, 103

[56] References Cited

U.S. PATENT DOCUMENTS 4,535,058 8/1985 Weinberg et al. ............... 436/813
4,699,877 10/1987 Cline et al. ........................ 435/6

OTHER PUBLICATIONS

Clark et al., Proc. Natl. Acad. Sci., USA, vol. 82, 1985, pp. 5280–5284.
Furth et al., Journal of Virology, vol. 43, No. 1, 1982, pp. 294–304.
Lacal et al., (1986) Cell 44:609–617.
Lacal et al., (1986) The EMBO Journal 5:679–687.
Lacal et al., (1986) Molecular and Cell. Biology 6:1002–1009.

Primary Examiner—Esther M. Kepplinger
Assistant Examiner—Florina B. Hoffer
Attorney, Agent, or Firm—Holman & Stern

[57] ABSTRACT

Specific deletion mutants of ras p21 gene and specific monoclonal antibodies which recognize specific regions of the ras p21 protein have been prepared. A kit for detecting the presence of specific ras p21 proteins and their levels in a body sample has been described.

7 Claims, 6 Drawing Sheets

HYDROPHILIC REGIONS

GTP-BINDING RELATED REGIONS

DELETION MUTANTS AND MONOCLONAL ANTIBODIES AGAINST RAS PROTEINS

BACKGROUND OF THE INVENTION

1. Technical Field

The present invention is related to the development of monoclonal antibodies against the ras p21 gene product and the use of genetically engineered deletion mutants to localize epitopes recognized by the antibodies. More particularly, the present invention is related to the use of monoclonals to dissect structural and functional properties of the oncogenic ras p21 protein and to detect ras p21 proteins in body tissue or body fluid as an indicator of the presence of malignant condition.

2. State of the Art

A small set of eukaryotic genes, termed proto-oncogenes, can be activated as oncogenes by a variety of mechanisms in naturally occurring tumor cells. These genes were initially detected as the transforming genes of retroviruses. Recent evidence has implicated their activation as oncogenes in as many as 10-30% of human malignancies by mechanisms involving point mutations at one of two major sites in their coding sequence (Capon et al., Nature 304: 507-513, 1983; Kraus et al., Proc. Natl. Acad. Sci. USA 81:5384-5388, 1984). The structural and functional characterization of ras genes has been significantly aided by expression of their p21 product at high levels in E. coli. Purification from bacterial extracts of normal and transforming p21s has also been successfully achieved (Lacal et al., Proc. Natl. Acad. Sci. USA 81:5305-5309, 1984; Stein et al., J. Virol. 50:343-351, 1984). Moreover, microinjection of low concentrations of the activated p21 product, or of much higher concentrations of normal p21, has been shown to induce morphological alterations as well as the induction of DNA synthesis in quiescent cells (Feramisco et al., Cell 38:109-117, 1984; Stacey and Kung, Nature 310:508-511, 1984).

In view of the importance of ras proto-oncogenes in the malignant process, there have been intensive investigations of the structure and function of p21 proteins. Biochemical activities associated with p21 proteins include GTP binding, GTP-dependent autophosphorylation and GTPase activities. Moreover, findings of some homology between ras proteins and known G proteins such as elongation factors and the α subunit of transducin suggest that the functions of p21 proteins are related to their ability to bind and hydrolyze GTP.

The ability of monoclonal antibodies to specifically recognize ras p21 proteins has provided essential tools for characterizing the processing, subcellular localization, and biochemical properties of the p21 molecule (Ulsh et al., Mol. Cell. Biol. 4:1647-1652, 1984).

To date, only a limited number of monoclonal antibodies have been generated against p21 (Furth et al., J. Virol 43:294-304, 1982) and their recognition sites on the p21 molecule have only been mapped in a very few cases.

SUMMARY OF THE INVENTION

It is, therefore, an object of the present invention to provide a series of monoclonal antibodies against p21 proteins which recognize defined regions of the p21 molecule and affect specific p21 functions.

It is another object of the present invention to provide specific deletion mutants of known sequence of the H-ras gene.

It is yet another object of the present invention to provide a method for detecting p21 proteins as indicators of malignancy or disease conditions related to abnormality in expression of p21 proteins utilizing the monoclonal antibodies developed.

A still further object of the present invention is to provide a kit comprising containers containing reagents, monoclonal antibodies, instructions and the like for detecting the p21 proteins in a body sample or in basic or applied research to study p21 structure-function relationships.

Other objects and advantages will become evident as the detailed description of the present invention proceed.

BRIEF DESCRIPTION OF DRAWINGS

These and other objects, features and many of the attendant advantages of the invention will be better understood upon a reading of the following detailed description when considered in connection with the accompanying drawings wherein.

DETAILED DESCRIPTION OF INVENTION

Figure 1:
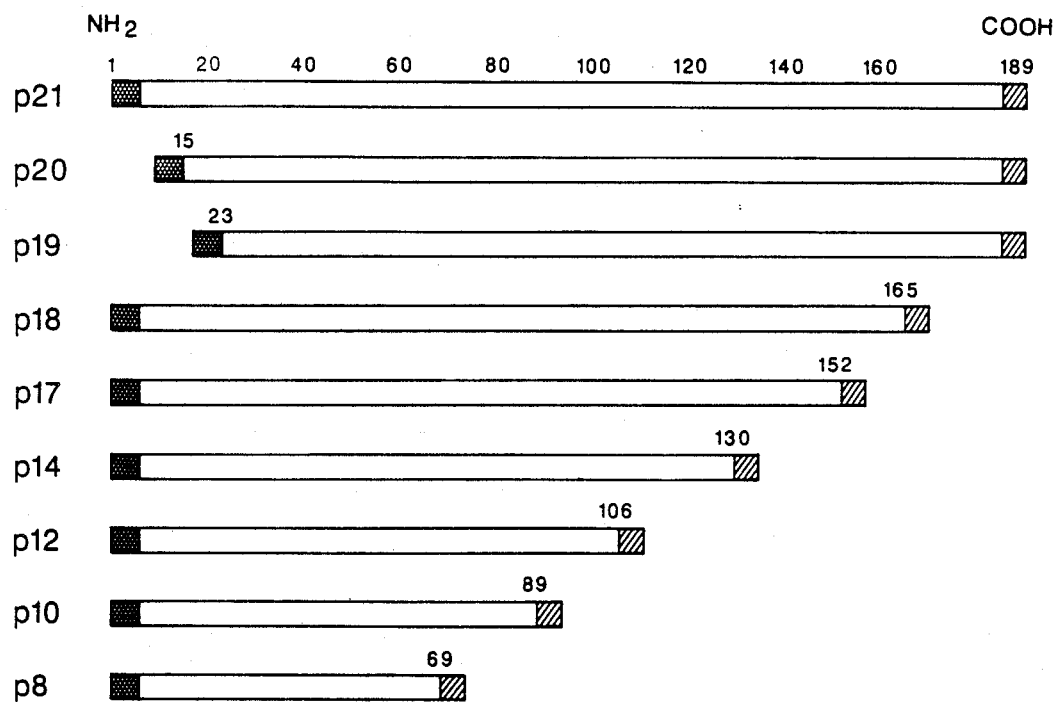
FIG. 1 is a schematic representation of ras p21 deletion mutants. The entire ras-coding sequence from the viral Havey gene was utilized to generate a series of deletion mutants. Restriction enzymes utilized for the genertion of each mutant were Pvu II for p19 and p20, Fok I for p18 (partial digestion) and p10, Ava II for p8, Hph I for p12, Hae III for p14, and Sfa NI for p17 (partial digestion). All generated mutants showed the first five amino acids at the amino terminus(▓▓▓▓▓▓▓▓), and the last four amino acids at the carboxy end(/////////////). The number above each construct indicates first or last amino acid present in the protein.

The above and various other objects and advantages of the present invention are achieved by specific deletion mutants, monoclonal antibodies and the kit of the present invention as described fully hereunder.

Unless defined otherwise, all technical or scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned hereunder are incorporated herein by reference.

MATERIALS AND METHODS

Bacterial strains. *E. coli* N4830 (PL Biochemicals, Inc.) was used for the epxression of the ras generated p21 products as described previously for *E. coli* strain RRI (Lacal et al., Proc. Natl. Acad. Sci. USA 81:5305–5309, 1984). The N4830 strain carries the temperature-sensitive C1857 gene and the N gene of a lambda lysogen to give a thermoinducible expression system.

Construction of p21 deletion mutants at the N terminus.

Plasmid pJCL-41 (FIG. 1) contains the complete, unfused gene encoding the ras p21 protein of Harvey murine sarcoma virus. After digestion, the HindIII insert of 850 bp contains the ras gene from amino acid 5 to 189 and additional viral sequences. The 4.5-kbp HindIII remaining plasmid contains the $P_L$ promoter from $\lambda$ phage, the appropriate ribosome binding site and the first four codons from the H-ras p21 protein coding for Met-Thr-Glu-Tyr. Further digestion of the 850-bp fragment with PvuII produced an ~800-bp fragment carrying the coding sequence of the H-ras p21 protein from codon 23 to 189. Synthetic linkers were then ligated to the PvuII site with T4 DNA ligase at a 100-fold molar excess linker:DNA fragment.

Construction of p21 deletion mutants at the C terminus.

The 850-bp HindIII fragment and the 4.5-kbp HindIII plasmid from PJCL-41 was isolated as indicated above. Digestion of the 850-bp HindIII fragment with HaeIII to completion and partially with SfaNI and FokI produced the carboxy ends

| 5′ CAGG 3′ | 5′CAG 3′ | 5′ACCA 3′ |
|---|---|---|
| 3′ GTCC 5 | 3′GTCCCAC 5′, | and 3′TGGTTCAG 5′, | respectively. After purification of fragments of 375 bp, 437 bp and 459 bp, synthetic linkers were ligated using T4 DNA ligase at a 100-fold molar excess linker:DNA fragment.

| Linker 1 was | CCAAGTGTGTGCTGTCCTGA GGTTCACACACGACAGGACTTCGA |
|---|---|
| Linker 2 was | GGTGTAAAGTGTGTGCTGTCCTGA ATTTCACACACGACAGGACTTCGA |
| Linker 3 was | AGTCCAAGTGTGTGCTGTCCTGA GTTCACACACGACAGGACTTCGA |
| Linker 4 was | GACAAGTGTGTGCTGTCCTGA TTCACACACGACAGGACTTCGA |
| Linker 5 was | AGTCCAAGTGTGTGCTGTCCTGA TTCACACACGACAGGACTTCGA |
| Linker 6 was | AAGTGTGTGCTGTCCTGA TTTCACACACGACAGGACTTCGA |

These linkers carry the coding sequence that restored the last four codons of the H-ras p21, the termination codon TGA and the sequence for HindIII. After digestion with HindIII, appropriate fragments were purified on agarose gels by electroelution and ligated to the 4.5-kpb HindIII fragment from PJCL-41. Analysis of the clones was carried out as described before (FIG. 1).

Plasmid constructions. The pRC23 plasmid, which carried the P promoter of lambda phage and a consensus ribosome binding site was obtained as described by Crowl et al., Gene 38:31–38, 1985. Digestion of DNAs was performed following supplier's instructions (New England Biolabs). Dephosphorylation of digested plasmids was carried out with calf intestine alkaline phosphatase (Boehringer) in 10 mM Tris-HCl, 10 mM $MgCl_2$, pH 8.5, for 1 h. Ligation of inserts to plasmids or synthetic linkers to DNA fragments was performed in 60 mM Tris-HCl, pH 7.6, 10 mM $MgCl_2$, 10 mM

| Linker A was | 5′ | AGCTTGTGGTGGTGGGCGCTAGAGGCGTG | 3′ |
|---|---|---|---|
| | 3′ | ACACCACCACCCGCGATCTCCGCAC | 5′ |
| Linker B was | 5′ | AGCTTGGAAAGAGTGCCCTGACCATCCAG | 3′ |
| | 3′ | ACCTTTCTCACGGGACTGGTAGGTC | 5′ |
| Linker C was | 5′ | AGCTTGCTAGAGGCGTGGGAAAGAGTGCC | 3′ |
| | 3′ | ACGATCTCCGCACCCTTTCTCACGG | 5′ |

Linker D, 5′ CCCAAGCTTGGG 3′ was obtained from PL Biochemicals (#7786). The four synthetic linkers were designed to restore the HindIII site at codon 5 and to carry different portions of the gene from positions 6 to 22 (linkers A, B and C) (see FIG. 3 for details) or to replace this region completely with the addition of a Gly in between (linker D). Positive clones were selected by hybridization utilizing the 850-bp HindIII fragment as probe. Restriction enzyme analysis with HindIII, EcoRI, PvuII and MstI enzymes allowed determination of the clones with the insert in the proper orientation.

DTT, 1 mM ATP, 1 mM spermidine and T4 DNA ligase at 14° C. for 14–16 h. Bacterial transformations were carried out as described by Lacal et al. Proc. Natl. Acad. Sci. USA 81:5305–5309, 1984. The construction of proteins p14, p17, p18, p19, and p20 was achieved as described by Lacal et al., Mol. Cell. Biol. 6:1002–1009, 1986. The construction of the deletion mutants p8, p10, and p12 was performed as described for p14 and p17 mutants. The 850-bp Hind III fragment was purified from the viral Harvey-ras p21 genome carrying the p21 ras sequences from codon 6 to 189 and additional viral sequences at the carboxy end. This fragment was then digested by Ava II, Fok I, or Hph I to generate smaller fragments of 210 bp (p8), 260 bp (p10), or 320 bp (p12) codifying for different regions of the p21 protein. After purification of the proper fragments, synthetic linkers designed to specifically restore the ends of the generated fragments, the last five amino acids of the ras p21 protein and a convenient Hind III site were ligated to them. Introduction in the proper orientation into adequate bacterial expression vectors gave vectors which expressed proteins of 8 kd (p8), 10 kd (p10), and 12 kd (p12), respectively. The sequence of these mutants were verified by DNA sequencing methods.

Protein expression and analysis. Bacterial cells containing ras gene expression vectors were grown in 10 ml of M9 salts supplemented with 0.5% casamino acids, 2% glucose, and 50 μg/ml ampicillin until a $A_{590}=0.2$ was reached. Cells were then centrifuged at 2500 rpm and changed to M9 salts without methionine, transferred to a 42° C. water-bath shaker and incubated for 5 min. [35S]-methionine (New England Nuclear, 800 Ci/m mol) was added to a final concentration of 50 μCi/ml and incubation proceeded for 1 h. After centrifugation at 2500 rpm for 10 min, cells were washed twice in 10 ml of 10 mM Tris-HC1, 1 mM EDTA, 100 mM NaCl, pH 7.5, and then sonicated for 30 seconds. Following centrifugation at 12,000 rpm for 10 min, ras p21 proteins were solubilized in 200 μl of 7M urea, 20 mM Tris-H Cl, pH 7.5, and ultracentrifuged in a Beckman airfuge for 10 min at $100,000 \times g$. Supernatants were collected and analyzed by sodium dodecylsulfate polyacrylamide gel electrophoresis (SDS-PAGE) or immunoprecipitation.

GTP-binding activity. The GTP-binding activity of highly purified p21 proteins was assayed by the amount of radioactivity retained in nitrocellulose filter (BA85, S & S) as described by Lacal et al., Cell 44: 609–617, 1986. When indicated, 25 ng of ras p21 proteins were incubated for 30 min at 0° C. with 500 ng of ammonium sulfate purified monoclonal antibodies in 200 μl GTP-binding buffer (50 mM Tris-H Cl, 10 mM $MgCl_2$, 2.5 mM DTT, 100 μg/ml bovine albumin), following which ($\alpha$-32P)GTP was added to a final concentration of 10 μM (ICN, 3000 μCi/mmol). Incubation at 37° C. proceeded for 15 min and samples filtered through BA85 filters, washed twice with 10 ml cold GTP-binding buffer, and the radioactivity retained by the filter was then determined in a scintillation counter.

When indicated, a second method was utilized to estimate the GTP binding of previously immunoprecipitated p21 proteins. In this procedure, 7M urea extracts of unlabeled p21 proteins were diluted 50 times in 200 μl of 10 mM sodium phosphate 1% Triton X-100, 0.1% SDS, 0.5% sodium deoxycholate, 1 mM phenylmethanesulfonyl fluoride, aprotinin (100 kalikrein inactivator units per ml), pH 7.4. Extracts were incubated for 30 min at 4° C. with different amounts of anti-Harvey-MSV p21 monoclonal antibodies, polyclonal antibody, or preimmune serum. Protein A-Sepharose was swollen and washed in the same buffer and coated with goat anti-rat IgG or goat anti-mouse IgG as described by Furth et al. (J. Virol. 43:294–304, 1982). 200 μl of a 1/10 (wt/vol) suspension of the coated protein A-Sepharose was added to each sample and the samples were shaken in an Eppendorf shaker at 4° C. for 15 min. Immunocomplexes were washed 3 times with the same buffer and the final pellets incubated in 200 μl of GTP-binding buffer containing 10 μM ($\alpha$-32P) GTP. Incubation for 45 min at 37° C. was carried out, samples were washed three times with cold GTP-binding buffer and the final pellets resuspended in 10 ml Aquasol and counted in a scintillation counter.

Monoclonal antibodies. Harvey-ras protein p21 ($Arg^{12}$-$Ala^{59}$) was expressed in E. coli and purified as mentioned herein above. After solubilization in 7 M urea, samples containing ~80% p21 were further purified through gel filtration in a Sephadex G-100. Fractions showing more than 95% purity for p21 were pooled, dialyzed against PBS and utilized for immunization into six female BALB/c mice. Immunization was carried out with 45 μg antigen/animal (150 μl each) with 150 μl complete Freund's adjuvant. Injections were performed into four sites, both axial and unguinal. Three more injections at 7, 14 and 21 days after the first injection were carried out with 15 μg antigen/animal in 150 μl incomplete Freund's adjuvant. Sera from each mouse were tested by immunoprecipitation to contain anti-p21 ras antibodies as indicated before. Mice were then exsanguinated and sera frozen at −20° C. for further analysis. Splenocytes were fused to P3X-63-Ag8-653 cells following standard techniques well known in the art and hybrids distributed into five-ten 96 well microtiter plates in Iscove's medium (Iscove et al., J. Exp. Med. 14:923–933, 1978) containing 10% fetal bovine serum and HAT medium (Littlefield, Science 145:709–712, 1964). Supernatant samples from microtiter plates were assayed for specific antibody production by enzyme-linked immunoadsorbant assay (ELISA) utilizing the Harvey-ras 21 molecule as antigen, and those scoring positive were cloned by limit dilution and analyzed by immunoprecipitation. Cell lines were grown in RPMI medium containing 10% serum (Colorado) until they reached $1-2 \times 10^6$ cell/ml. After washing twice with RPMI medium without serum, cells were resuspended in 3–4 times the original volume of RPMI medium without serum and incubated at 37° C. for 2–3 days. Cells were removed by centrifugation and antibodies precipitated by addition of ammonium sulfate to 50% (331 g/l). After dialysis against PBS, antibodies were stored at −20° C. prior to use. Polyclonal antibody was obtained from New Zealand white rabbits immunized with purified Harvey-ras p21 protein by peripheral node injection in Freund's complete adjuvant, followed by subcutaneous injection in Freund's incomplete adjuvant two weeks later. Three additional subcutaneous booster injections were given at two-week intervals. Blood samples were taken one week after injection, and processed as described for monoclonal antibodies.

Figure 2:
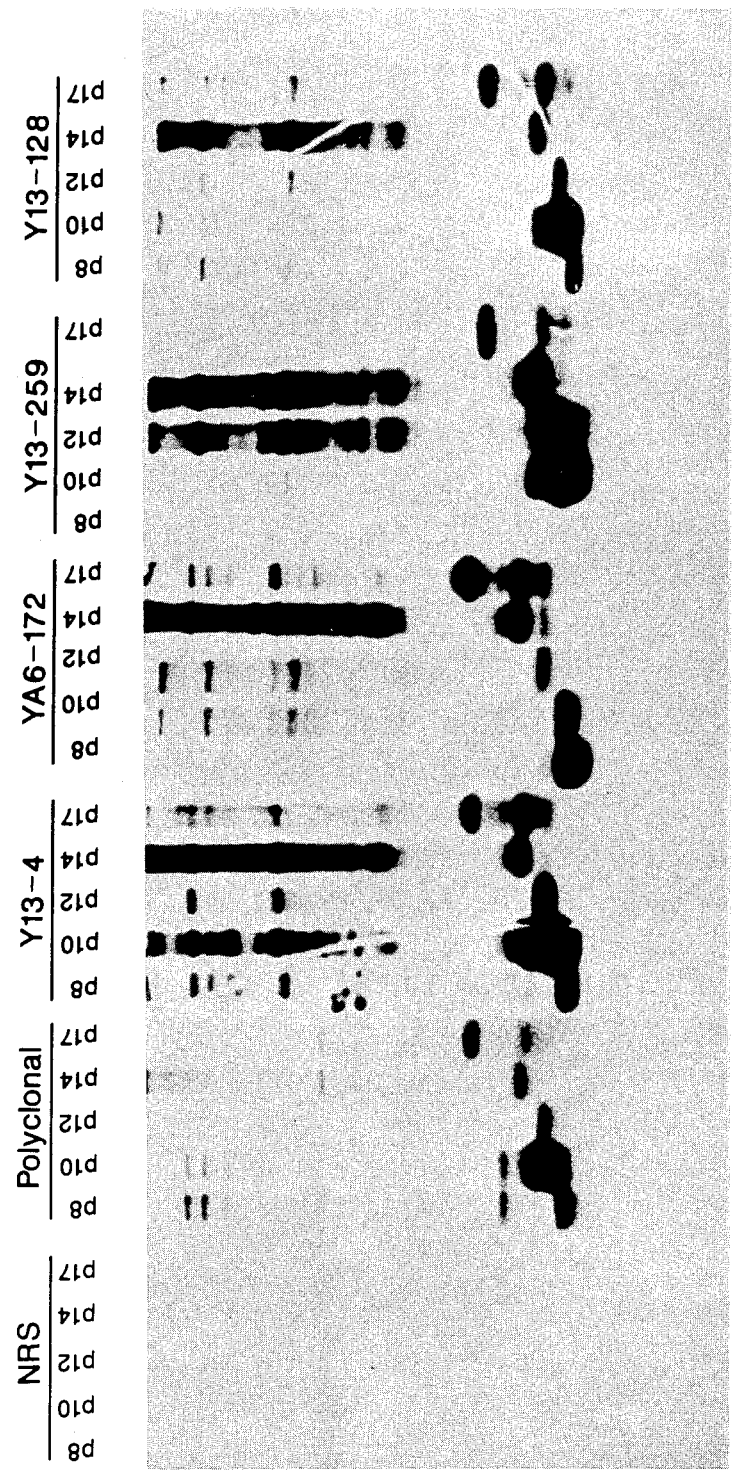
FIG. 2 shows immunoprecipitation of ras p21 deletion mutants by monoclonal antibodies. Equal amounts of (35S)-met labeled extracts from bacterial clones expressing p8, p10, p12, p14, and p17 were immunoprecipitated by equivalent amounts of a rabbit polyclonal antibody against p21, or the monoclonal antibodies Y13-4, YA6-172, Y13-259, and Y13-128. As a negative control, a preimmune rat serum was utilized (NRS). Similar results were obtained when preimmune rabbit sera were utilized.

FIG. 1 shows the predicted structures of polypeptides encoded by the various ras deletion mutants. The protein encoded by each mutant was shown to react with polyclonal antibody directed against ras p21 and demonstrated the expected size (FIG. 2). Moreover, the sequence of each mutant was confirmed by DNA sequencing.

Of course, the present series of p21 deletion mutants were designed as part of a strategy to localize epitopes recognized by the monoclonal antibodies raised against p21 so that functional domains within the p21 molecule could be determined. This enables the identification of epitopes localized within amino acid sequences from 1–15, 16–23, 24–69, 70–89, 90–106, 107–130, 131–152, 153–165, and 166–189 of the p21 molecule.

As shown in Table 1, the antibodies generated by the present invention showed different patterns of reactivity against the series of p21 deletion mutants utilized as radiolabeled antigens in immunoprecipitation studies.

The most abundant group contained those able to recognize all of the deletion mutants which shared amino acids 1–5, 23–69, and 184–189. Monoclonals within this group, including M8 and M9, were further tested and shown to immunoprecipitate p21 mutants lacking amino acids 1–5 and 184–189 (data not shown) indicating that the epitopes recognized by these monoclonals are within the region from amino acids 23 to 69. Other monoclonals recognized regions of the p21 molecule within amino acids 1–23, 90–106, 107–130, or 131–152 (Table 1). These findings suggest that the monoclonals recognize six defined regions of the p21 molecule.

TABLE 1

Monoclonal antibodies mapping within the ras p21 molecule

| Antibody | p21 | p20 | p19 | p8 | p10 | p12 | p14 | p17 | p18 |
|---|---|---|---|---|---|---|---|---|---|
| M8 | + | + | + | + | + | + | + | + | + |
| M11 | + | + | + | + | + | + | + | + | + |
| M13 | + | + | + | + | + | + | + | + | + |
| M15 | + | + | + | + | + | + | + | + | + |
| M17 | + | + | + | + | + | + | + | + | + |
| M19 | + | + | + | + | + | + | + | + | + |
| M20 | + | + | + | + | + | + | + | + | + |
| M21 | + | + | + | + | + | + | + | + | + |
| M22 | + | + | + | + | + | + | + | + | + |
| M23 | + | + | + | + | + | + | + | + | + |
| M24 | + | + | + | + | + | + | + | + | + |
| M25 | + | + | + | + | + | + | + | + | + |
| M26 | + | + | + | + | + | + | + | + | + |
| M27 | + | + | + | + | + | + | + | + | + |
| M33 | + | + | + | + | + | + | + | + | + |
| M37 | + | + | + | + | + | + | + | + | + |
| M56 | + | + | + | + | + | + | + | + | + |
| M9 | + | +/− | + | + | + | + | + | + | + |
| M28 | + | +/− | + | + | + | + | + | + | + |
| M42 | + | +/− | + | + | + | + | + | + | + |
| M49 | + | +/− | + | + | + | + | + | + | + |
| M53 | + | +/− | + | + | + | + | + | + | + |
| M38 | + | +/− | − | + | + | + | + | + | + |
| M91 | + | +/− | − | + | + | + | + | + | + |
| M94 | + | +/− | − | + | + | + | + | + | + |
| M70 | + | + | + | − | − | + | + | + | + |
| M92 | + | + | + | − | − | + | + | + | + |
| M96 | + | + | + | − | − | + | + | + | + |
| M97 | + | + | + | − | − | + | + | + | + |
| M100 | + | + | + | − | − | + | + | + | + |
| M103 | + | + | + | − | − | + | + | + | + |
| M104 | + | + | + | − | − | + | + | + | + |
| M90 | + | + | + | − | − | − | + | + | + |
| M3 | + | + | + | − | − | − | − | + | + |
| M30 | + | + | + | − | − | − | − | + | + |
| M43 | + | + | + | − | − | − | − | + | + |
| M44 | + | + | + | − | − | − | − | + | + |
| M50 | + | + | + | − | − | − | − | + | + |
| M57 | + | + | + | − | − | − | − | + | + |
| M58 | + | + | + | − | − | − | − | + | + |
| M66 | + | + | + | − | − | − | − | + | + |
| Polyclonal | + | + | + | + | + | + | + | + | + |

The list of the 42 newly generated IgG monoclonal antibodies against the ras p21 protein is related. The results obtained by regular immunoprecipitations of $^{35}$S-met bacterial extracts from each ras p21 derivative as described in Methods, are inclusive. Recognition levels camparable to those of a polyclonal antibody against the complete p21 protein able to recognize all deletion mutants is indicated as (+). When the antibody failed to recognize the protein, it is indicated as (−). When recognition was substantially lower than that of polyclonal antibody, it is indicated as (+/−).

TABLE 2

GTP-binding activity of p21 after immunoprecipitation by monoclonal antibody

| Antibody | First Immunoprecipitate | Second Immunoprecipitate |
|---|---|---|
| NRS | 4105 | 245,110 |
| Polyclonal | 5525 | 11,320 |
| Y13-4 | 271,195 | 10,050 |
| 713-128 | 262,125 | 9880 |
| Y13-259 | 302,080 | 9945 |
| YAG-172 | 306,715 | 5900 |
| M3 | 4830 | 2390 |
| M8 | 6790 | 3630 |
| M9 | 8880 | 5200 |
| M38 | 5380 | 8340 |
| M70 | 253,340 | 4361 |
| M90 | 2735 | 5150 |

Approximately 1 pmol of highly purified Harvey ras p21 protein was immunoprecipitated by an excess (500 ng) of monoclonal or polyclonal antibodies as indicated in Methods. Supernatants of the immunoprecipitates were then treated with equal amounts (500 ng) of monoclonal antibody Y13-259 and both first and second immunoprecipitates were analyzed for GTP-binding activity as described in Methods. One pmol of ($\alpha$-$^{32}$P) GTP was equivalent to 6.67 × 10$^5$ cpm.

TABLE 3

Immunoprecipitation of [p21-GTP] complex by monoclonal antibodies

| Antibody | Amount (ng) | [p21-GTP] complex (cpm) |
|---|---|---|
| NRS | 200 | 645 |
| | 500 | 1465 |
| Polyclonal | 200 | 10,745 |
| | 500 | 18,450 |
| Y13-4 | 200 | 205,890 |
| | 500 | 191,860 |
| Y13-128 | 200 | 175,365 |
| | 500 | 181,635 |
| Y13-259 | 200 | 196,780 |
| | 500 | 194,855 |
| YAG-172 | 200 | 217,725 |
| | 500 | 205,465 |
| M3 | 200 | 1320 |
| | 500 | 3705 |
| M8 | 200 | 7620 |
| | 500 | 12,070 |
| M9 | 200 | 4275 |
| | 500 | 2695 |
| M38 | 200 | 1530 |
| | 500 | 2395 |
| M70 | 200 | 189,100 |
| | 500 | 170,435 |
| M90 | 200 | 1220 |
| | 500 | 3020 |

Highly purified Harvey ras p21 protein was incubated for 60 min in GTP-binding buffer containing 10 μM ($\alpha$-32P) GTP. After incubation, protein samples were aliquoted in 1 pmol aliquots and different amounts of antibody added to each sample. Immunoprecipitation proceeded as described in Methods, and determination of the [p21-GTP] complex, estimated by scintillation counter. One pmol of ($\alpha$-$^{32}$p)-GTP, was equivalent to 6.7 × 10$^5$ cpm.

The hybridomas which produce monoclonal antibodies designated M8, M30, M38, M70 and M90 have been deposited in ATCC, Rockville, Md., as a single combined deposit from which each individual hybridoma can be isolated and grown separately employing standard techniques well known in the art to which the present invention belongs. The ATCC deposit number is HB9158.

M38 recognizes sequences between residues 1-23 of the ras p21 molecule;

M8 recognizes sequences between residues 24-69 of the ras p21 molecule;

M70 recognizes sequences between residues 90-106 of the ras p21 molecule;

M90 recognizes sequences between residues 107-130 of the ras p21 molecule;

M30 recognizes sequences between residues 131-152 of the ras p21 molecule;

The deletion mutants of the present invention, prepared and maintained as plasmids which are propagated in *E. coli*, have also been deposited at ATCC, Rockville, Md. as a single combined deposit from which each individual mutant can be isolated and propagated employing standard techniques well known in the art to which the present invention belongs. The ATCC deposit number is 67170. These deletion mutants of the ras p21 gene and the amino acid residues which they encode are as follows.

p20: encoding 1 to 5 and 15 to 189 amino acid residues
p19: encoding 1 to 5 and 23 to 189 amino acid residues
p18: enclinding 1 to 165 and 185 to 189 amino acid residues
p17: encoding 1 to 152 and 185 to 189 amino acid residues
p14: encoding 1 to 130 and 185 to 189 amino acid residues
p12: encoding 1 to 106 and 185 to 189 amino acid residues
p10: encoding 1 to 89 and 185 to 189 amino acid residues
p8: encoding 1 to 69 and 185 to 189 amino acid residues It is noted that the deposits made at the ATCC shall be viably maintained for the life of the patent if issued, or for at least 30 years from the date of the deposit and made available without restriction to the public upon issuance of the patent, of course, consistent with the provisions of the law.

Determination of the domains of the ras p21 protein related to its GTP-binding function.

Figure 4:
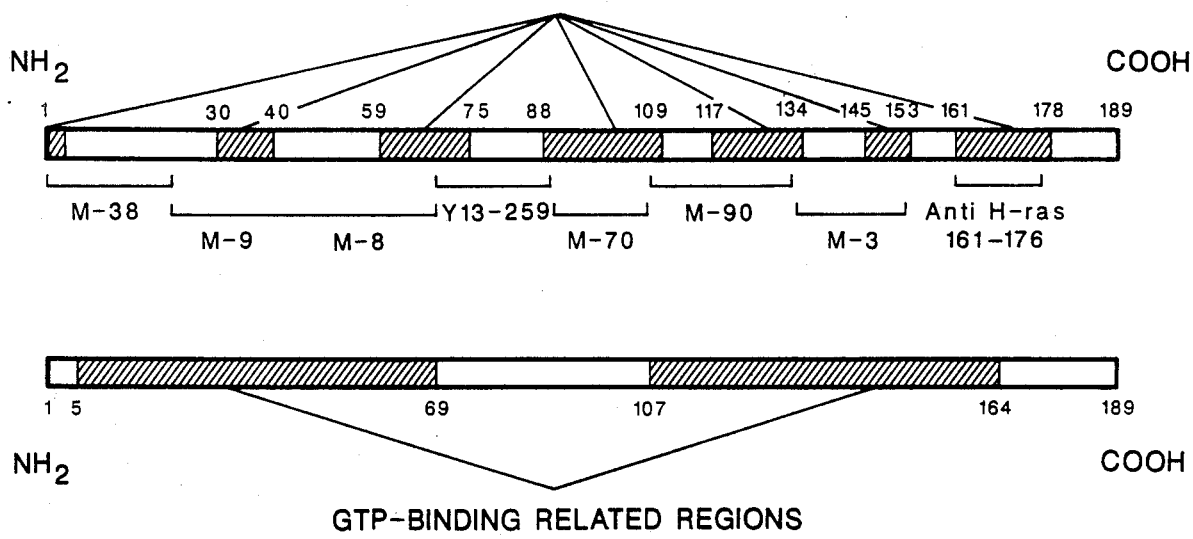
FIG. 4 schematic representation of epitope mapping data and hypothetical hydrophilic regions of ras p21 proteins. The entire p21 molecule is represented showing the different epitopes recognized by various monoclonal antibodies including M38, M9, M8, M70, M90 and M3. Hydrophilic regions of the ras p21 molecule are indicated in the upper schema as striped boxes(/////////////). These regions comprise the extreme amino terminus, amino acid sequences from 30 to 40, 59 to 75, 88 to 109, 117 to 134, 145 to 153, and 161 to 178. The lower schema depicts those regions that are related to the GTP-binding site as striped boxes(▨), including amino acids 5 to 69 and 107 to 164.
Figure 3:
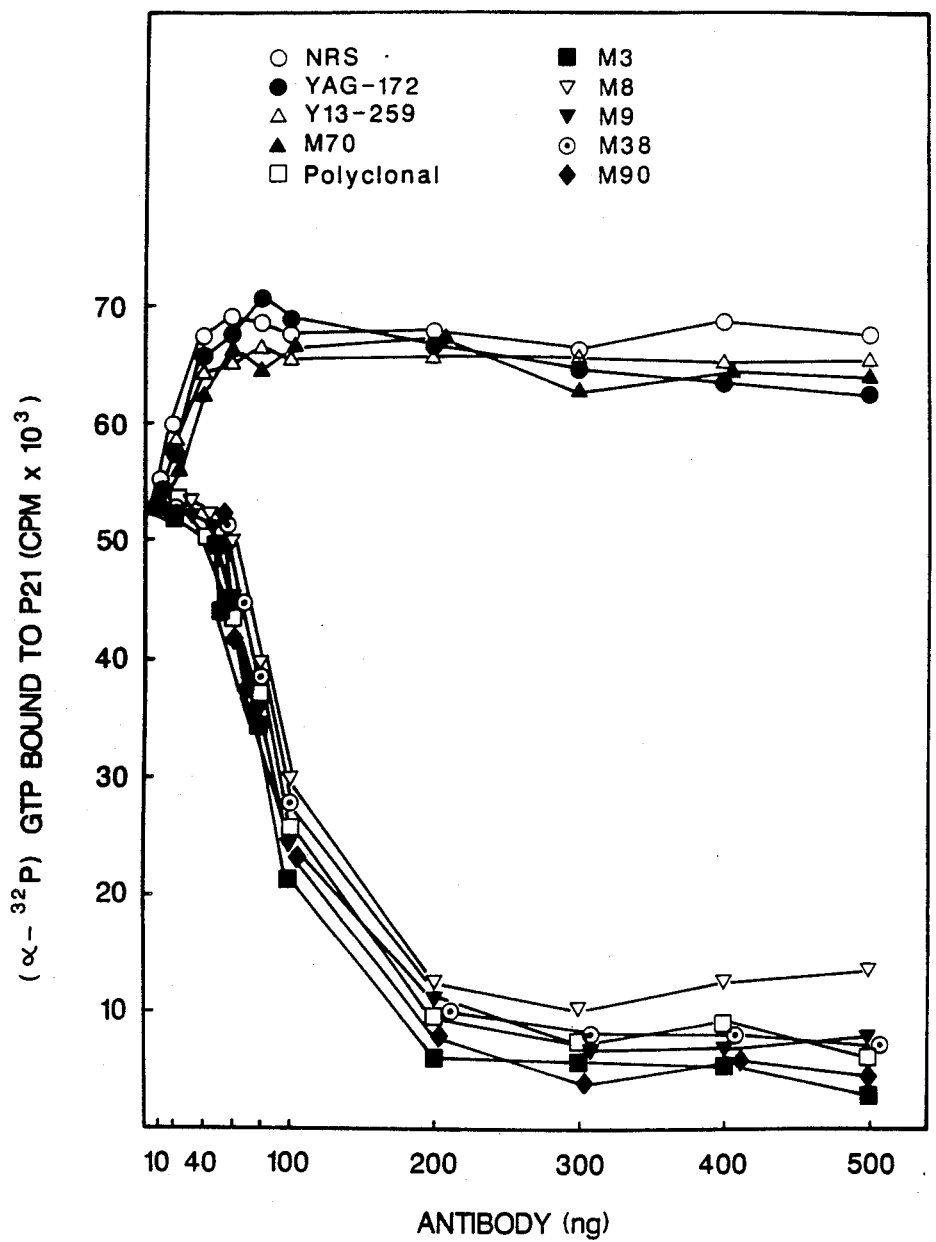
FIG. 3 shows effect on GTP binding activity of p21 by various antibodies. Approximately 25 ng of highly purified viral Harvey-ras p21 protein (~1.2 pmol) were incubated with different amount of each monoclonal or polyclonal antibody up to a molar ratio of 2.8-fold antibody to p21. After preincubation with the antibody, the GTP-binding activity of the p21 protein was determined by filter assay. Considering that the antibody is a bifunctional molecule, the actual ratio of binding sites to p21 molecules was 5.6-fold. One pmol of (α-32P) GTP was equivalent to 96,300 cpm.
Figure 5A:
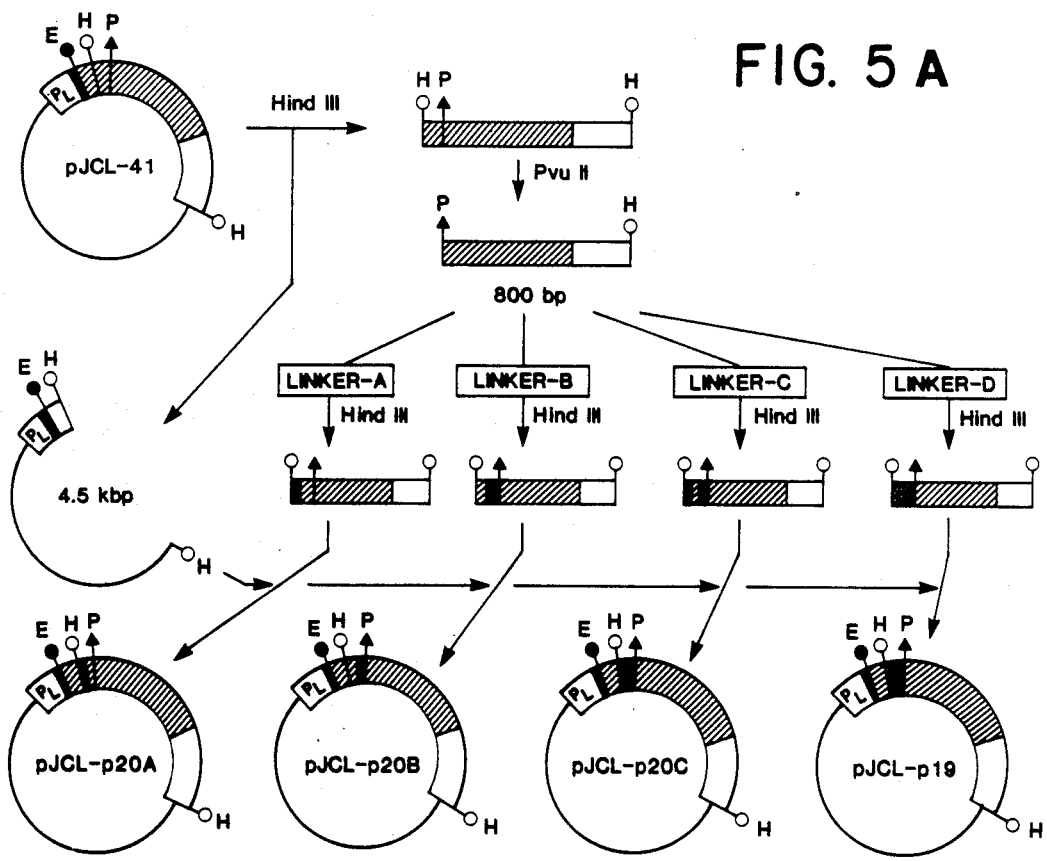
FIG. 5 shows the construction of p21 deletion mutants at the N terminus.
Figure 5B:
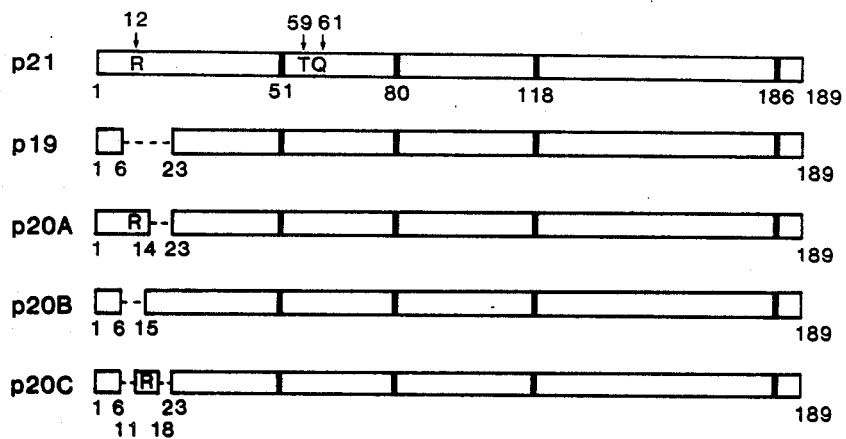
Figure 6A:
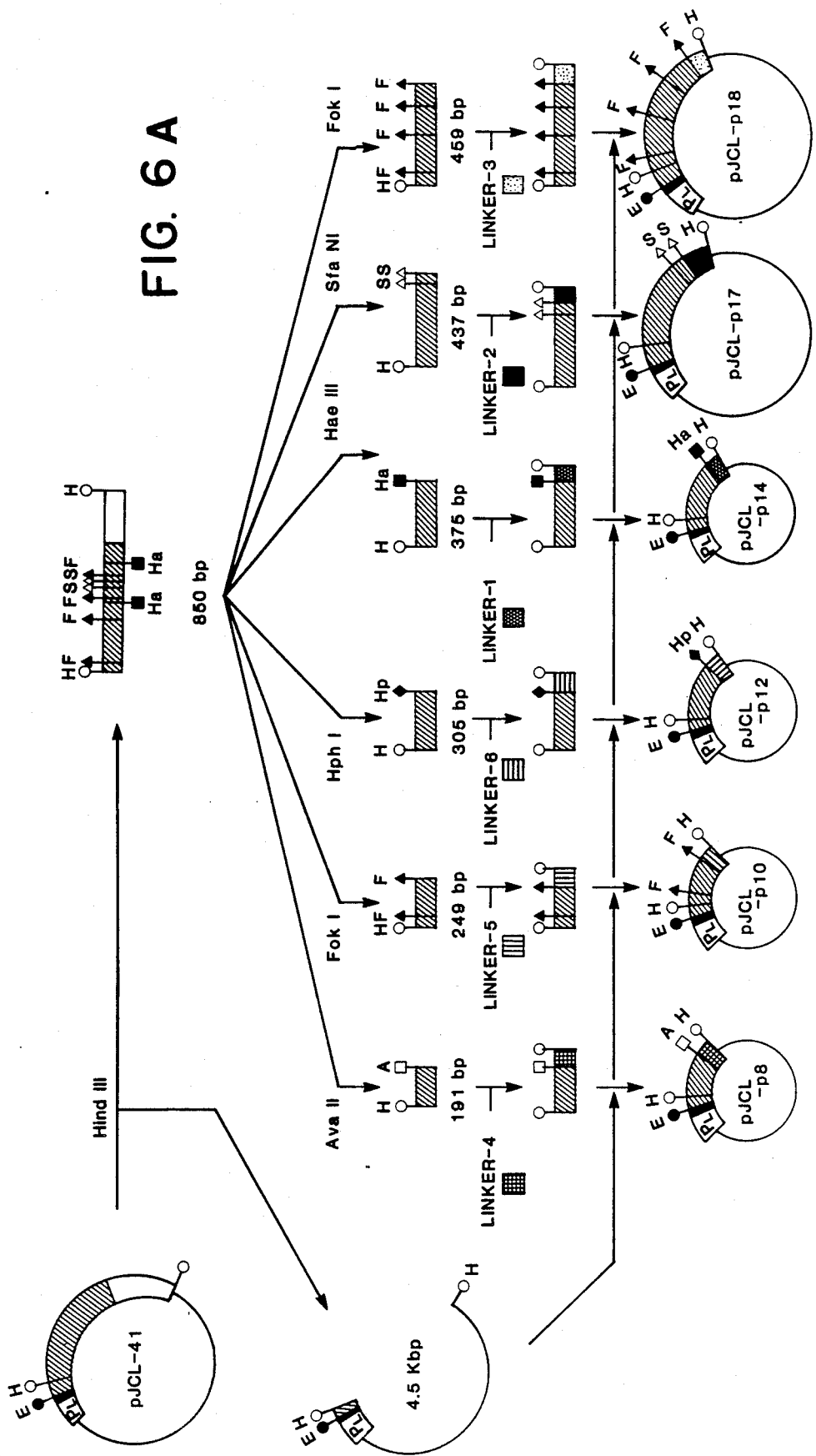
FIG. 6 shows the construction of p21 deletion mutants at the C terminus.
Figure 6B:
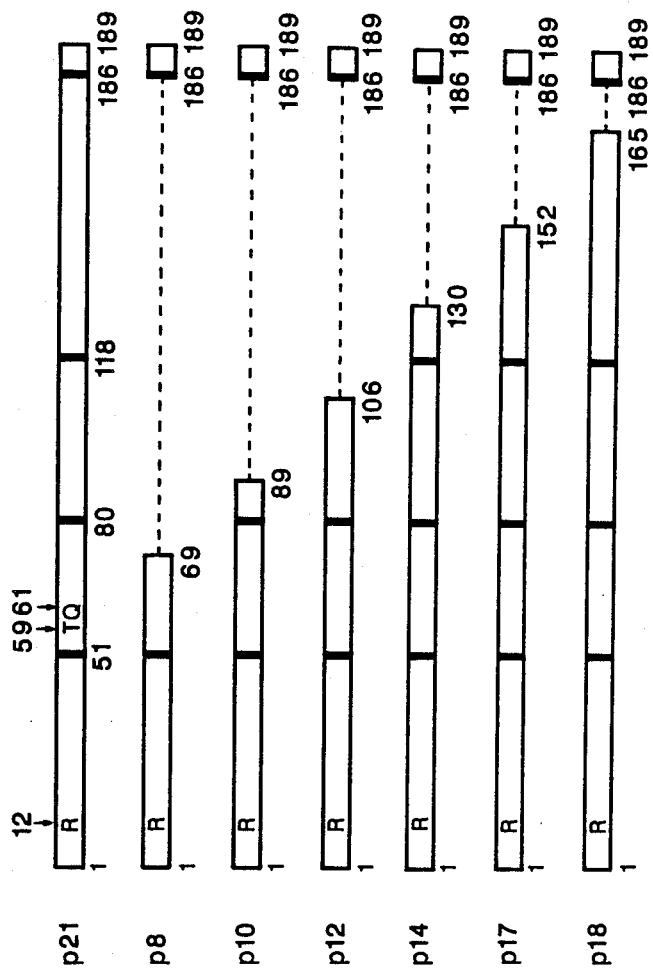

In order to assess the effect of monoclonals directed against different regions of the p21 molecule on its functional properties, the ability of representatives of each monoclonal group to interfere with GTP-binding by p21 was tested. Following preincubation with different antibody concentrations, the ability of p21 to bind radiolabeled GTP was determined as described herein supra. The amount of [GTP-p21]-complex formed was measured in solution by a nitrocellulose filter assay. As shown in FIG. 4, monoclonals M3, M8, M9, and M38 and M90 as well as polyclonal antibody against p21 produced a drastic inhibition of GTP-binding activity. In contrast, incubation with up to a 5-fold molar excess of monoclonal antibodies M70, Y13-259, Y13-4, Y13-128, or YA6-172 produced no inhibition of this activity when compared to the effects of preimmune serum (FIG. 3).

The ability of the same monoclonals to inhibit GTP binding following imunoprecipitation of p21 under conditions of antibody excess (Table 2) was also determined. Monoclonal antibodies M3, M8, M9, M38, and M90 as well as the polyclonal antibody were able to immunoprecipitate all active p21 molecules and to completely block GTP binding of the immunoprecipitated proteins, while antibodies Y13-259, Y13-4, Y13-128, YA6-172, and M70 failed to inhibit this activity. Thus, the results of two different approaches for identification of monoclonals capable of blocking GTP binding by p21 were in complete agreement.

It was possible that if a particular monoclonal antibody inhibited the GTP-binding property of ras p21, the [p21-GTP] complex might not be recognized by that antibody due to interference of GTP with the epitope. To test this possibility, about 1 pmole of p21 was incubated with 10 $\mu$M ($\alpha$-32P)-GTP in GTP-binding buffer followed by immunoprecipitation with an excess of each monoclonal antibody. As shown in Table 3, antibodies M3, M8, M9, M38, and M90 and the polyclonal antibody failed to efficiently immunoprecipitate the [p21-GTP] complex, whereas monoclonals Y13-259, Y13-4, Y13-128, YA6-172 and M70 all readily reocgnized the same complex. These findings indicate the existence of two major classes of monoclonals, those which do and those which do not interfere with the GTP-binding function of the p21 molecule.

The results of the tests described herein establish that the GTP-binding function of p21 is drastically impaired in deletion mutants wherein the coding sequences proximal to amino acid 165 were removed, while a p21 derivative with amino acids 1-165 retained full GTP-binding activity. Furthermore, deletions of very small stretches at the amino terminus of the molecule, from position 5 to 23, were enough to eliminate GTP-binding activity, while a p21 fusion protein in which the first 4 amino acids were substituted by 8 amino acids encoded by the expression vector exhibited GTP-binding activity. These findings indicate the localization of GTP-binding regions of the p21 molecule from amino acids 5 to 69 and 107 to 164, respectively (FIG. 4).

These results further establish that the monoclonal antibodies of the present invention interfere with the GTP-binding ability of the corresponding proteins. In contrast, none of the monoclonal antibodies obtained by Furth et al. (J. Virol. 43:294-304, 1982) interfered directly with this activity. Without being bound to any theory, this difference may be explained by the fact taht the earlier series of monoclonals was obtained from tumor-bearing rats. In the tumor cell, p21 is likely to be associated with guanine nucleotide, blocking exposure of p21 antigenic determinants involved in nucleotide binding. In the system of the present invention, bacterially expressed p21 was purified by a method which yielded virtually nucleotide-free p21, exposing those determinants involved in GTP-binding. The lack of recognition of a deletion mutant defines the missing sequences as essential for antibody detection of the protein. The generation of this new series of monoclonals which recognize a range of epitopes throughout the p21 molecule now makes it possible to more definitively characterize the structure and functional properties of the ras gene products. For instance, the monoclonal antibodies of the present invention can be used in a kit comprising containers containing monoclonal antibodies of the present invention, cryopreserved if necessary in a buffered medium (such as phosphate buffer or physiologicsl saline and the like), unequivocally detecting and distinguishing the presence of the type and amounts of the p21 proteins from other similar proteins or antigens. Since p21 proteins are also indicators of the oncogenes, the determination of the type and level of p21 proteins in a body sample can also be used for detecting cancers or other diseases related to p21 gene-activation. The kit also contains instructions to perform the test, which essentially comprises immunodetection techniques well known in the art.

It is understood that the examples and embodiments described herein are for illustrative purposes only and that various modifications or changes in light thereof will be suggested to persons skilled in the art and are to be included within the spirit and purview of this application and the scope of the appended claims.

We claim:

1. Monoclonal antibodies which recognize specific regions of ras p21 molecule wherein said regions are involved in GTP-binding, said monoclonal antibodies being selected from the group consisting of M38 (ATTC HB 9158) which recognizes amino acid sequence comprising residues 1-23; M8 (ATCC HB 9158) which recognizes amino acid sequence comprising residues 24–69; M70 (ATCC HB 9158) which recognizes amino acid sequence comprising residues 90–106; M90 (ATCC HB 9158) which recognizes amino acid sequence comprising residues 107–130; M30 (ATCC HB 9158) which recognizes amino acid sequence between residues 131–152; and a combination thereof.

2. The monoclonal antibody of claim 1 having the identifying characteristics of M38 ATCC HB 9158.

3. The monoclonal antibody of claim 1 having the identifying characteristics of M8 ATCC HB 9158.

4. The monoclonal antibody of claim 1 having the identifying characteristics of M70 ATCC HB 9158.

5. The monoclonal antibody of claim 1 having the identifying characteristics of M90 ATCC HB 9158.

6. The monoclonal antibody of claim 1 having the identifying characteristics of M30 ATCC HB 9158.

7. A kit for detecting the presence of ras p21 protein comprising containers separately containing monoclonal antibodies of claim 1.

* * * * *